United States Patent [19]
Behr et al.

[11] Patent Number: 6,013,240
[45] Date of Patent: Jan. 11, 2000

[54] NUCLEIC ACID CONTAINING COMPOSITION, PREPARATION AND USES OF SAME

[75] Inventors: Jean-Paul Behr, Strasbourg; Barbara Demeneix, Paris; Franck Lezoualch, Paris; Mojgan Mergny, Ivry Sur Seine; Daniel Scherman, Paris; Otmane Boussif, Strasbourg, all of France

[73] Assignee: Rhone-Poulenc Rorer SA, Anthony Cedex, France

[21] Appl. No.: 08/765,679

[22] PCT Filed: Jul. 7, 1995

[86] PCT No.: PCT/FR95/00914

§ 371 Date: Feb. 28, 1997

§ 102(e) Date: Feb. 28, 1997

[87] PCT Pub. No.: WO96/02655

PCT Pub. Date: Feb. 1, 1996

[30] Foreign Application Priority Data

Jul. 13, 1994 [FR] France .................................... 94/08735

[51] Int. Cl.⁷ ...................................................... A61K 9/127
[52] U.S. Cl. .................. 424/1.21; 435/6; 514/44
[58] Field of Search ................................... 435/6; 514/44; 264/4.1; 424/1.21, 450

[56] References Cited

FOREIGN PATENT DOCUMENTS

| 0424688 | 5/1991 | European Pat. Off. . |
|---|---|---|
| WO91/16024 | 10/1991 | WIPO . |
| WO93/05162 | 3/1993 | WIPO . |
| WO93/20090 | 10/1993 | WIPO . |
| WO94/01448 | 1/1994 | WIPO . |
| WO94/05624 | 3/1994 | WIPO . |

*Primary Examiner*—Scott W. Houtteman
*Attorney, Agent, or Firm*—Martin F. Savitzky; Raymond S. Parker, III

[57] ABSTRACT

Compositions containing one or more nucleic acids and cationic polymers, and their use in gene therapy, particularly for in vivo nucleic acid transfer.

34 Claims, 11 Drawing Sheets

NUCLEIC ACID CONTAINING COMPOSITION, PREPARATION AND USES OF SAME

The present invention relates to compositions based on nucleic acids, to their preparation and to their use. More especially, it relates to compositions comprising at least one nucleic acid and some cationic polymers, and to their use for the transfer of nucleic acids into cells, in particular in gene therapy.

Gene therapy consists in correcting a deficiency or an abnormality (mutation, aberrant expression, and the like) or in effecting the expression of a protein of therapeutic value by introducing genetic information into the affected cell or organ. This genetic information may be introduced either in vitro into a cell extracted from the organ, the modified cell then being reintroduced into the body, or directly in vivo into the appropriate tissue. Different techniques have been described for transferring this genetic information, including various transfection techniques involving complexes of DNA and DEAE-dextran (Pagano et al., J. Virol. 1 (1967) 891), of DNA and nuclear proteins (Kaneda et al., Science 243 (1989) 375), of DNA and lipids (Felgner et al., PNAS 84 (1987) 7413) and of DNA and polylysine, the use of liposomes (Fraley et al., J. Biol. Chem. 255 (1980) 10431), and the like. More recently, the use of viruses as vectors for gene transfer has been seen to be a promising alternative to these physicochemical transfection techniques. In this connection, different viruses have been tested for their capacity to infect certain cell populations. In particular, retroviruses (RSV, HMS, MMS, and the like), the HSV virus, adeno-associated viruses and adenoviruses may be mentioned.

However, the techniques developed hitherto do not enable the difficulties associated with gene transfer into cells and/or the body to be resolved satisfactorily. In particular, the problems associated with the entry of nucleic acid into cells are not completely solved. In effect, the polyanionic nature of nucleic acids, in particular, prevents their passage through cell membranes. While it has been shown that naked nucleic acids are capable of passing through the plasma membrane of some cell types in vivo (see, in particular, Application No. WO90/11092), the efficiency of transfection remains rather low. Furthermore, naked nucleic acids have a short plasma half-life on account of their degradation by enzymes and their elimination in the urine. Moreover, while recombinant viruses enable the efficiency of transfer of nucleic acids to be improved, their use presents some risks, such as pathogenicity, transmission, replication, recombination, transformation, immunogenicity, and the like. Furthermore, their production according to the specifications of Good Manufacturing Practice presents some difficulties.

The present invention provides an advantageous solution to these different problems. The Applicant has, in effect, shown that some cationic polymers possess especially advantageous properties for the transfer of nucleic acid into cells, both in vitro and in vivo. In addition, these polymers have the advantage of being readily accessible and inexpensive. The use of cationic polymers according to the invention also enables the drawbacks associated with the use of viral vectors (potential dangers, limited size of the gene transferred, higher cost, and the like), to be avoided.

More especially, the present invention lies in the demonstration of the transfecting properties of the polymers of formula (I):

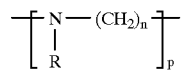
(I)

in which
R can be a hydrogen atom or a group of formula

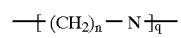

n is an integer between 2 and 10;
p and q are integers, on the understanding that the sum p+q is such that the average molecular weight of the polymer is between 100 and $10^7$ Da.

It is understood that, in the formula (I), the value of n can vary between the different units p. Thus, the formula (I) embraces both homopolymers and heteropolymers.

A first subject of the invention is therefore a composition comprising at least one nucleic acid and a cationic polymer of general formula (I) as defined above.

The invention also relates to the use of the cationic polymers of formula (I) for the transfer of is nucleic acids into cells.

More preferably, in the formula (I), n is between 2 and 5. In particular, polyethylenimine (PEI) and polypropylenimine (PPI) polymers have altogether advantageous properties.

Preferred polymers for carrying out the present invention are those whose molecular weight is between $10^3$ and $5 \times 10^6$. As an example, there may be mentioned polyethylenimine of average molecular weight 50,000 Da (PEI50K) or polyethylenimine of average molecular weight 800,000 Da (PEI800K).

The polymers used in the context of the present invention may be obtained in different ways. They may, in the first place, be synthesized chemically from the corresponding monomer under anionic polymerization conditions (for example polymerization of ethylenimine), or by reduction of polyamides obtained by polycondensation of diacids with diamines, or alternatively by reduction of imines obtained by polycondensation of dialdehydes with diamines. Moreover, a number of these polymers are commercially available, such as, in particular, PEI50K or PEI800K.

To obtain an optimum effect of the compositions of the invention, the respective proportions of the polymer and the nucleic acid are preferably determined in such a way that the mole ratio R=polymer amines/nucleic acid phosphates is between 0.5 and 50, and more preferably between 5 and 30. Most especially advantageous results are obtained using from 5 to 15 equivalents of polymer amines per nucleic acid charge. This ratio may naturally be adapted by a person skilled in the art in accordance with the polymer used, the presence of an adjuvant (see below), the nucleic acid, the target cell and the mode of administration used.

In the compositions of the present invention, the nucleic acid can be either a deoxyribonucleic acid or a ribonucleic acid. The sequences in question can be of natural or artificial origin, and in particular genomic DNA, cDNA, mRNA, tRNA, rRNA, hybrid sequences or synthetic or semi-synthetic sequences. In addition, the nucleic acid can be very variable in size, ranging from oligonucleotide to chromosome. These nucleic acids may be of human, animal, vegetable, bacterial, viral, and the like, origin. They may be obtained by any technique known to a person skilled in the art, and in particular by the screening of libraries, by chemical synthesis or alternatively by mixed methods including the chemical or enzymatic modification of sequences obtained by the screening of libraries. They can, moreover, be incorporated into vectors, such as plasmid vectors.

As regards, more especially, deoxyribonucleic acids, the latter may be single- or double-stranded. These deoxyribonucleic acids can carry therapeutic genes, sequences regulating transcription or replication, antisense sequences, regions for binding to other cell components, and the like.

For the purposes of the invention, therapeutic gene is understood, in particular, to mean any gene coding for a proteinaceous product having a therapeutic effect. The proteinaceous product thus encoded can be a protein, a peptide, and the like. This proteinaceous product can be homologous with respect to the target cell (that is to say a product which is normally expressed in the target cell when the latter is not suffering from any pathology). In this case, the expression of a protein makes it possible, for example, to remedy an insufficient expression in the cell or the expression of a protein which is inactive or feebly active on account of a modification, or alternatively to overexpress the said protein. The therapeutic gene may also code for a mutant of a cell protein, having enhanced stability, modified activity, and the like. The proteinaceous product may also be heterologous with respect to the target cell. In this case, an expressed protein may, for example, supplement or supply an activity which is deficient in the cell, enabling it to combat a pathology, or stimulate an immune response. The therapeutic gene may also code for a protein secreted into the body.

Among therapeutic products for the purposes of the present invention, there may be mentioned, more especially, enzymes, blood derivatives, hormones, lymphokines, namely interleukins, interferons, TNF, and the like (FR 92/03120), growth factors, neurotransmitters or their precursors or synthetic enzymes, trophic factors, namely BDNF, CNTF, NGF, IGF, GMF, aFGF, bFGF, NT3, NT5, HARP/pleiotrophin, and the like; apolipoproteins, namely ApoAI, ApoAIV, ApoE, and the like (FR 93/05125), dystrophin or a minidystrophin (FR 91/11947), the CFTR protein associated with cystic fibrosis, tumor-suppressing genes, namely p53, Rb, Rap1A, DCC, k-rev, and the like (FR 93/04745), genes coding for factors involved in coagulation, namely factors VII, VIII, IX, genes participating in DNA repair, suicide genes (thymidine kinase, cytosine deaminase), and the like.

The therapeutic gene can also be an antisense gene or sequence, whose expression in the target cell enables the expression of genes or the transcription of cellular mRNAs to be controlled. Such sequences can, for example, be transcribed in the target cell into RNAs complementary to cellular mRNAs and can thus block their translation into protein, according to the technique described in Patent EP 140,308. Other possible sequences include synthetic oligonucleotides, optionally modified (EP 92,574). Antisense sequences also comprise sequences coding for ribozymes, which are capable of selectively destroying target RNAs (EP 321,201).

As stated above, the nucleic acid can also contain one or more genes coding for an antigenic peptide capable of generating an immune response in man or animals. In this particular embodiment, the invention hence makes possible the production either of vaccines or of immunotherapeutic treatments applied to man or animals, in particular against microorganisms, viruses or cancers. Such peptides include, in particular, antigenic peptides specific to the Epstein Barr virus, the HIV virus, the hepatitis B (EP 185,573) or the pseudorabies virus, or alternatively tumor-specific peptides (EP 259,212).

Preferably, the nucleic acid also comprises sequences permitting the expression of the therapeutic gene and/or of the gene coding for the antigenic peptide in the desired cell or organ. These sequences can be the ones which are naturally responsible for expression of the gene in question when these sequences are capable of functioning in the infected cell. They can also be sequences of different origin (responsible for the expression of other proteins, or even synthetic sequences). In particular, they can be promoter sequences of eukaryotic or viral genes. For example, they can be promoter sequences originating from the genome of the cell which it is desired to infect. Similarly, they can be promoter sequences originating from the genome of a virus. In this connection, the promoters of the E1A, MLP, CMV, RSV and the like, genes may, for example, be mentioned. In addition, these expression sequences may be modified by the addition of activation or regulatory sequences or sequences permitting a tissue-specific expression.

Moreover, the nucleic acid can also contain, especially upstream of the therapeutic gene, a signal sequence directing the therapeutic product synthesized into the pathways of secretion of the target cell. This signal sequence can be the natural signal sequence of the therapeutic product, but it can also be any other functional signal sequence, or an artificial signal sequence.

Moreover, in addition, the nucleic acid can also contain, especially upstream of the therapeutic gene, a sequence directing the therapeutic product synthesized towards a preferential cellular compartment, such as a nuclear localization sequence.

The compositions according to the invention may be used as they are or in combination with other compounds. Thus, in a particular embodiment, the compositions according to the present invention comprise, in addition, an adjuvant capable of combining with the polymer/nucleic acid complex and of improving the transfecting power. The Applicant has, in effect, shown that the transfecting power of the compositions of the invention may be further improved in the presence of certain adjuvants (lipids, proteins, lipopolyamines, synthetic polymers, for example) capable of combining with the polymer/nucleic acid complex. As shown in the examples of the present application, this improvement manifests itself both in vitro and in vivo.

The adjuvants used preferentially in the compositions according to the invention are cationic lipids (containing one or more cationic charges in their polar portion) or neutral lipids.

As regards cationic lipids, they can be, more especially, lipopolyamines, that is to say any amphiphilic molecule comprising at least one polyamine hydrophilic region and one lipophilic region which are bound covalently to one another via a chemical arm. Advantageously, the polyamine region of the lipopolyamines used in the context of the invention corresponds to the general formula $H_2N-(-(CH)_m-NH-)_l-H$, in which m is an integer greater than or equal to 2 and l is an integer greater than or equal to 1, it being possible for m to vary between the different carbon groups lying between two amines. Preferably, m is between 2 and 6 inclusive and l is between 1 and 5 inclusive. Still more preferably, the polyamine region is represented by spermine or a spermine analogue which has retained its properties of binding to DNA.

The lipophilic region can be one or several saturated or unsaturated hydrocarbon chains, cholesterol, a natural lipid or a synthetic lipid, capable of forming lamellar or hexagonal phases.

Advantageously, lipopolyamines as are defined in Patent Application EP 394,111 are used in the context of the present invention. That application also describes a process which can be used for the preparation of these lipopolyamines. In the context of the invention, it is especially advantageous to use dioctadecylamidoglycylspermine (DOGS) or palmitoylphosphatidylethanolamine 5-carboxyspermylamide (DPPES).

Other adjuvants which are especially preferred for producing the compositions of the invention are represented by neutral lipids. The use of neutral lipids is especially advantageous when the (amines/phosphates) charge ratio R is low. More preferably, the neutral lipids used in the context of the present invention are lipids containing 2 fatty chains.

It is especially advantageous to use natural or synthetic lipids which are zwitterionic or which lack ionic charge under physiological conditions. It may be chosen, more especially, from dioleoylphosphatidylethanolamine (DOPE), oleoylpalmitoylphosphatidylethanolamine (POPE), distearoyl-, -palmitoyl- and -myristoylphosphatidylethanolamine as well as their 1- to 3-fold N-methylated derivatives; phosphatidylglycerols, diacylglycerols, glycosyldiacylglycerols, cerebrosides (such as, in particular, galactocerebrosides), sphingolipids (such as, in particular, sphingomyelins) or alternatively asialogangliosides (such as, in particular, asialoGM1 and -GM2).

These different lipids may be obtained either synthetically or by extraction from organs (for example the brain) or eggs, by standard techniques well known to a person skilled in the art. In particular, the extraction of natural lipids may be carried out by means of organic solvents (see also Lehninger, Biochemistry).

Preferably, the compositions of the invention comprise, in addition to the cationic polymer in the ratios mentioned above, from 0.1 to 20 molar equivalents of adjuvant per molar equivalent of nucleic acid phosphate, and more preferably, from 1 to 5.

In an especially advantageous embodiment, the compositions of the present invention comprise a targeting element enabling the transfer of the nucleic acid to be guided. This targeting element can be an extracellular targeting element, enabling the transfer of the nucleic acid to be guided towards certain cell types or certain desired tissues (tumor cells, liver cells, haematopoietic cells, and the like). It can also be an intracellular targeting element, enabling the transfer of the nucleic acid to be guided towards certain favored cellular compartments (mitochondria, nucleus, and the like).

More preferably, the targeting element is bound covalently or non-covalently to the polymer of formula (I). The binding can, in particular, be obtained by ionic interaction with the ammonium groups, or by nucleophilic attack of the polymer amines on targeting elements containing a nucleofugal group (halogen, tosylate, and the like), an activated ester (hydroxysuccinimide, and the like) or alternatively an isothiocyanate. The targeting element can also be bound to the nucleic acid.

Among targeting elements which can be used in the context of the invention, sugars, peptides, oligonucleotides or lipids may be mentioned. Preferably, these elements are sugars and/or peptides, such as antibodies or antibody fragments, cell receptor ligands or fragments thereof, receptors or receptor fragments, and the like. In particular, they can be ligands for growth factor receptors, for cytokine receptors, for cellular lectin receptors or for adhesion protein receptors. The transferrin, HDL and LDL receptor may also be mentioned. The targeting element can also be a sugar enabling the asialoglycoprotein receptors to be targeted, or alternatively an antibody Fab fragment enabling the immunoglobulin Fc fragment receptor to be targeted.

The compositions according to the invention may be formulated with a view to topic, cutaneous, oral, rectal, vaginal, parenteral, intranasal, intravenous, intramuscular, subcutaneous, intraocular, transdermal, and the like, administration. Preferably, the pharmaceutical compositions of the invention contain a vehicle which is pharmaceutically acceptable for an injectable formulation, in particular for direct injection into the desired organ, or for a topical administration (to skin and/or mucosa). The products in question can be, in particular, isotonic sterile solutions, or dry, in particular lyophilized, compositions which, on addition of sterilized water or physiological saline as appropriate, enable injectable solutions to be formed. The doses of nucleic acid used for the injection, as well as the number of administrations, may be adapted in accordance with different parameters, and in particular in accordance with the mode of administration used, the pathology in question, the gene to be expressed or alternatively the desired period of treatment.

As stated above, the compositions according to the invention can be used for the transfer of nucleic acids into cells in vivo, in vitro or ex vivo. In particular, the examples show that the cationic polymers of the invention may be used to transfer nucleic acids very efficiently into many cell types, and especially into certain cell types which are usually difficult to transfect. Among the cell types tested, fibroblasts, liver cells, carcinomas, kidney cells and neurons may be mentioned in particular. In addition, the examples presented below also illustrate the efficacy of the polymers of the invention for the transfer of genes in vivo. The results obtained with the vectors of the invention are superior to those observed under the same conditions with other transfecting agents, and thus demonstrate the high potentialities of the compositions of the invention.

The present invention provides, in particular, an especially advantageous method for the treatment of disorders, comprising the in vivo administration of a nucleic acid capable of correcting the said disorder, combined with a cationic polymer as is defined above. More especially, this method is applicable to disorders resulting from a deficiency of a proteinaceous or nucleic acid product, and the nucleic acid administered codes for the said proteinaceous product or contains the said nucleic acid product.

The pharmaceutical compositions of the invention thus constitute especially advantageous tools for the administration and transfer of nucleic acids in vivo.

The present invention will be described more completely by means of the examples which follow, which are to be considered as illustrative and non-limiting.

EXAMPLE 1

Figure 1:
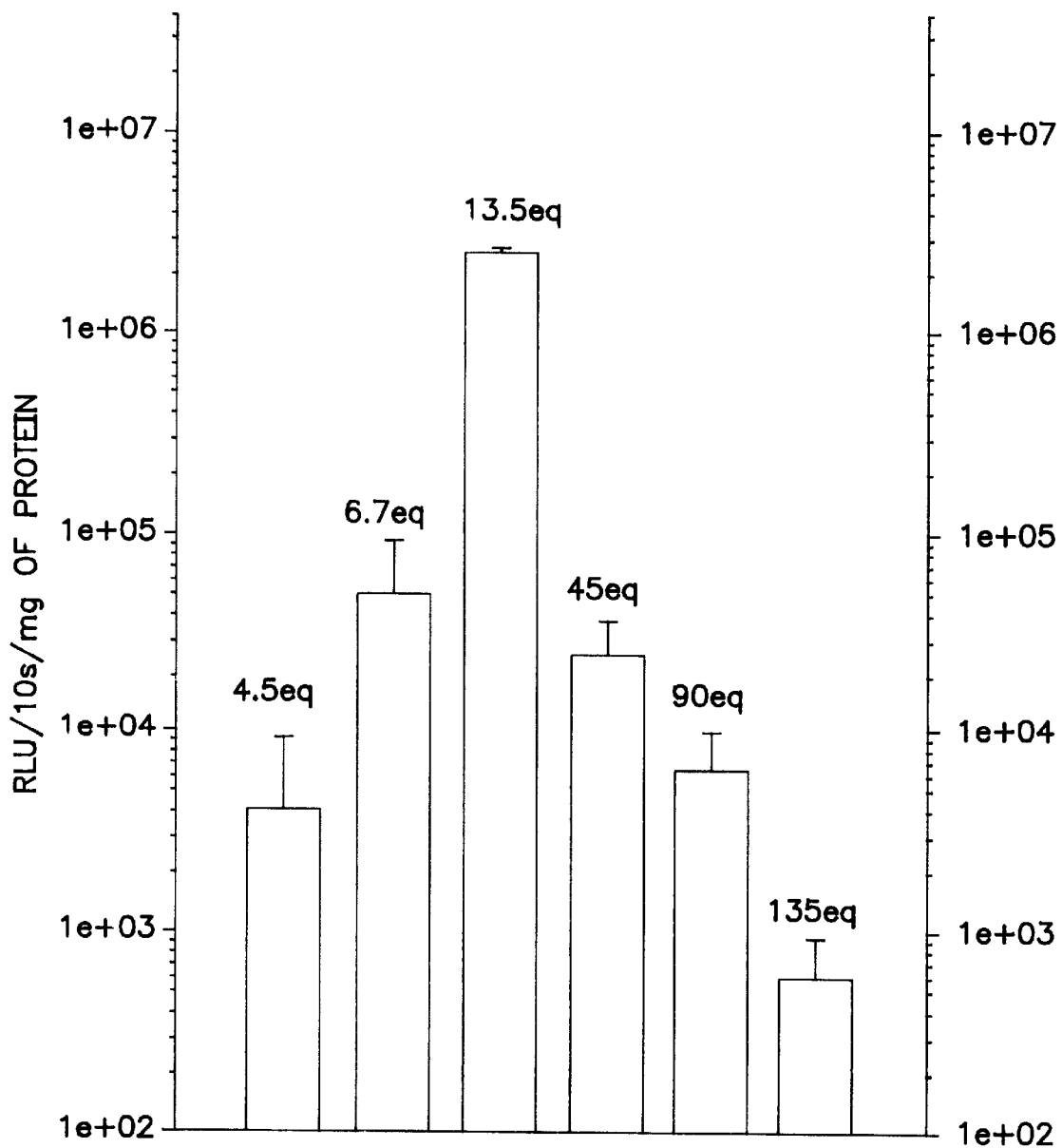
FIG. 1: Efficiency of transfection of PEI800K at pH7 in terms of the (polymer amines/nucleic acid phosphates) ratio R

Plasmids Used for in vivo Gene Transfer

Three types of constructions were used to demonstrate the activity of the compositions of the invention: plasmids containing the gene coding for luciferase (Luc), plasmids containing the gene coding for β-galactosidase (LacZ gene) and plasmids containing the gene coding for chloramphenicol acetyltransferase (CAT).

1.1. Plasmids Containing the Luc Gene

The plasmid pCMV-luc contains the cytomegalovirus (CMV) promoter, extracted from the vector plasmid pcDNA3 (Invitrogen) by cleavage with the restriction enzymes MluI and HindIII, located upstream of the gene coding for luciferase, inserted at the MlUI and HindIII sites into the vector pGL basic Vector (Promega).

The plasmid pGL2-Luc is of commercial origin (Promega).

The plasmid T3RE-Luc contains a synthetic oligonucleotide corresponding to a palindromic element for response to thyroid hormone (Glass et al., Cell 56 (1989) 697).

1.2. Plasmids Containing the LacZ Gene

The plasmid pCMV-βGal (Clontech) contains the CMV promoter located upstream of the LacZ gene coding for β-galactosidase of *Escherichia coli*. The vector pSV-nls LacZ (pAOnlsLacZ) contains the same promoter, a nuclear localization sequence (originating from the SV40 virus) localized in frame and upstream of the LacZ gene. This construction permits the expression of the fusion protein nls-β-galactosidase in the nucleus of the cells (see De Luze et al., PNAS 90 (1993) 7322).

1.3. Plasmids containing the CAT gene

Plasmids having as reporter gene the gene coding for chloramphenicol acetyltransferase (CAT) under the control of the RSV promoter (pRSV-CAT) and SV40 promoter (pSV40-CAT) have been published (Boutiller et al., Prog. Neuro-PhychoPharmacol. et Biol. Psychiat. 16 (1992) 959; de Luze et al. PNAS 90 (1993) 7322).

EXAMPLE 2

Transfer of Nucleic Acid into Fibroblasts

This example describes the transfer of plasmid pGL2-luc into 3T3 fibroblasts by means of 800,000 Da polyethylenimine.

Protocol: A 5.375 $\mu$M solution of PEI800K is prepared, and the pH is adjusted to 7 using 1 N hydrochloric acid solution. This solution is used for the gene transfer experiments.

Transfection protocol: 3T3 fibroblasts are inoculated into a 24-well dish 24 hours before transfection (50,000 cells per well). They are transfected with 2 $\mu$g of plasmid pGL2-Luc per well according to the following protocol:

2 $\mu$g of plasmid and different volumes of the 5.375 $\mu$M solution of PEI800K (depending on the desired charge equivalent ratio) are diluted separately in 50 $\mu$l of 150 mM Nacl and mixed. After 10 minutes, the two solutions are combined and homogenized. After a further period of 10 minutes, 900 $\mu$l of DMEM are added. The solution thereby obtained is homogenized and, after 10 minutes, it is distributed on cells previously rinsed with DMEM medium without serum. After 2 hours of transfection, 100 $\mu$l of FCS (foetal calf serum) are added per well. Expression is stopped 24 hours later.

Luciferase assay: For this purpose, the supernatant was incubated in the presence of a buffer comprising the luciferin, coenzyme A and ATP, and the light emitted (generally for 10 seconds) was measured with a luminometer (Wood K. (1990) Promega Notes, 28).

The results obtained are presented in FIG. 1. They show that PEI enables plasmid pGL2-Luc to be transferred efficiently into fibroblasts. They also show that the activity in relative light units (RLU) is especially good when between 5 and 20 equivalents of PEI amines are used relative to the DNA phosphates. In a controlled experiment, the plasmid alone gives a signal of approximately 100 RLU.

EXAMPLE 3

Effect of the Amount of DNA on the Efficiency of Transfection

This example describes the effect of the amount of nucleic acid on the efficiency of transfer into 3T3 fibroblasts by PEI800K.

3T3 fibroblasts are inoculated into a 24-well dish 24 hours before transfection (50,000 cells per well). They are transfected with increasing amounts of plasmid pCMV-Luc per well and a constant charge ratio (9 equivalents), according to the protocol described previously. Two points have been produced by making up the amount of plasmid to two $\mu$g per well with plasmid pGEM (PROMEGA) not containing the gene under study. After 3 hours of transfection, 100 $\mu$l of FCS serum is added per well. Expression is stopped 24 hours later.

Figure 2:
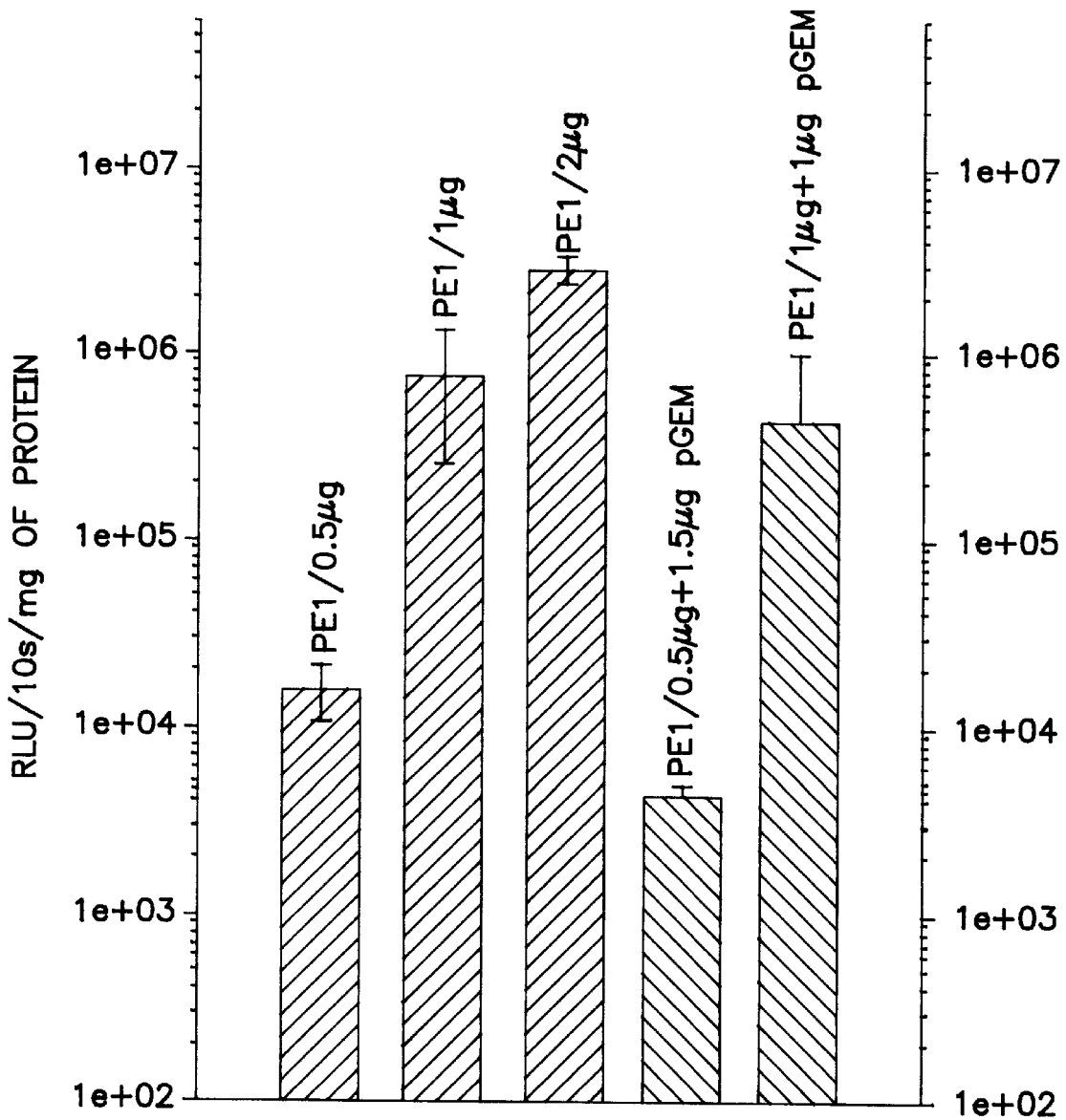
FIG. 2: Efficiency of transfection of PEI500K at pH6 in terms of the amount of DNA

The results obtained are shown in FIG. 2.

The efficiency of transfection increases with the amount of plasmid used during transfection. The addition of untranscribed carrier DNA (pGEM) makes no contribution to transfection.

EXAMPLE 4

Transfer of Nucleic Acids into Fibroblasts: Study of the Influence of the Amines/Phosphates Ratio This example describes the transfer of nucleic acids into fibroblasts at pH 6 by means of a composition according to the invention comprising nucleic acid and PEI800K in different (amines/phosphates) ratios R.

Protocol: A 5.375 $\mu$M solution of PEI800K is prepared, and the pH is adjusted to 6 using 1 N hydrochloric acid solution. This solution is used for the gene transfer experiments.

3T3 fibroblasts are inoculated into a 24-well dish 18 hours before transfection (50,000 cells per well). They are transfected with 2 $\mu$g of plasmid pGL2-Luc per well according to the protocol used in Example 2.

Figure 3:
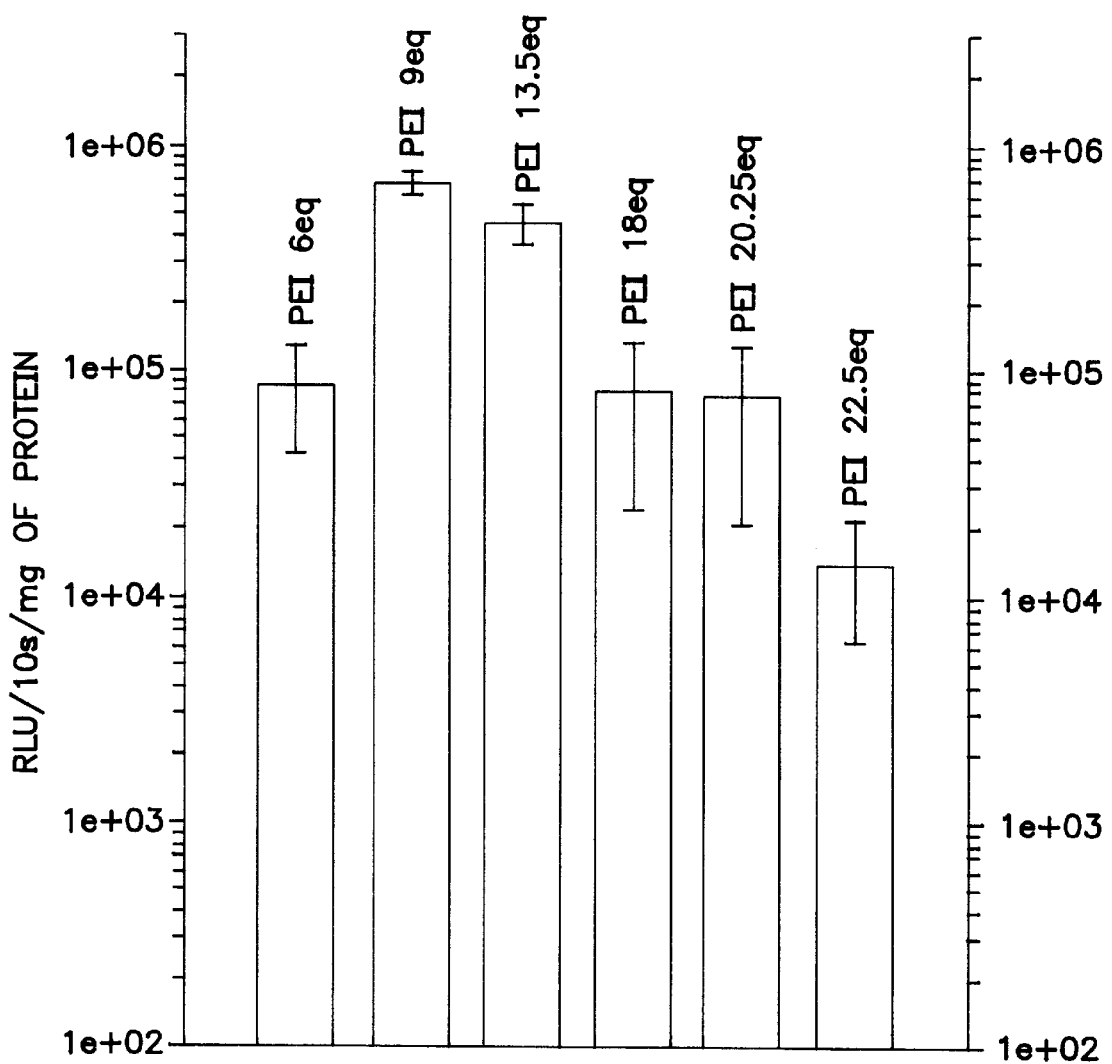
FIG. 3: Efficiency of transfection of PEI800K at pH6 in terms of the ratio R

The results obtained are presented in FIG. 3. They show that the compositions according to the invention are especially efficient over a whole range of ratios R of between 6 and 22.

EXAMPLE 5

Efficiency of Transfection in Terms of pH

This example describes the transfer of nucleic acids into fibroblasts by means of a composition according to the invention comprising nucleic acid and PEI800K under different pH conditions.

The protocol used is identical to that described in Example 2. The pH is adjusted by adding 1 N hydrochloric acid.

Figure 4:
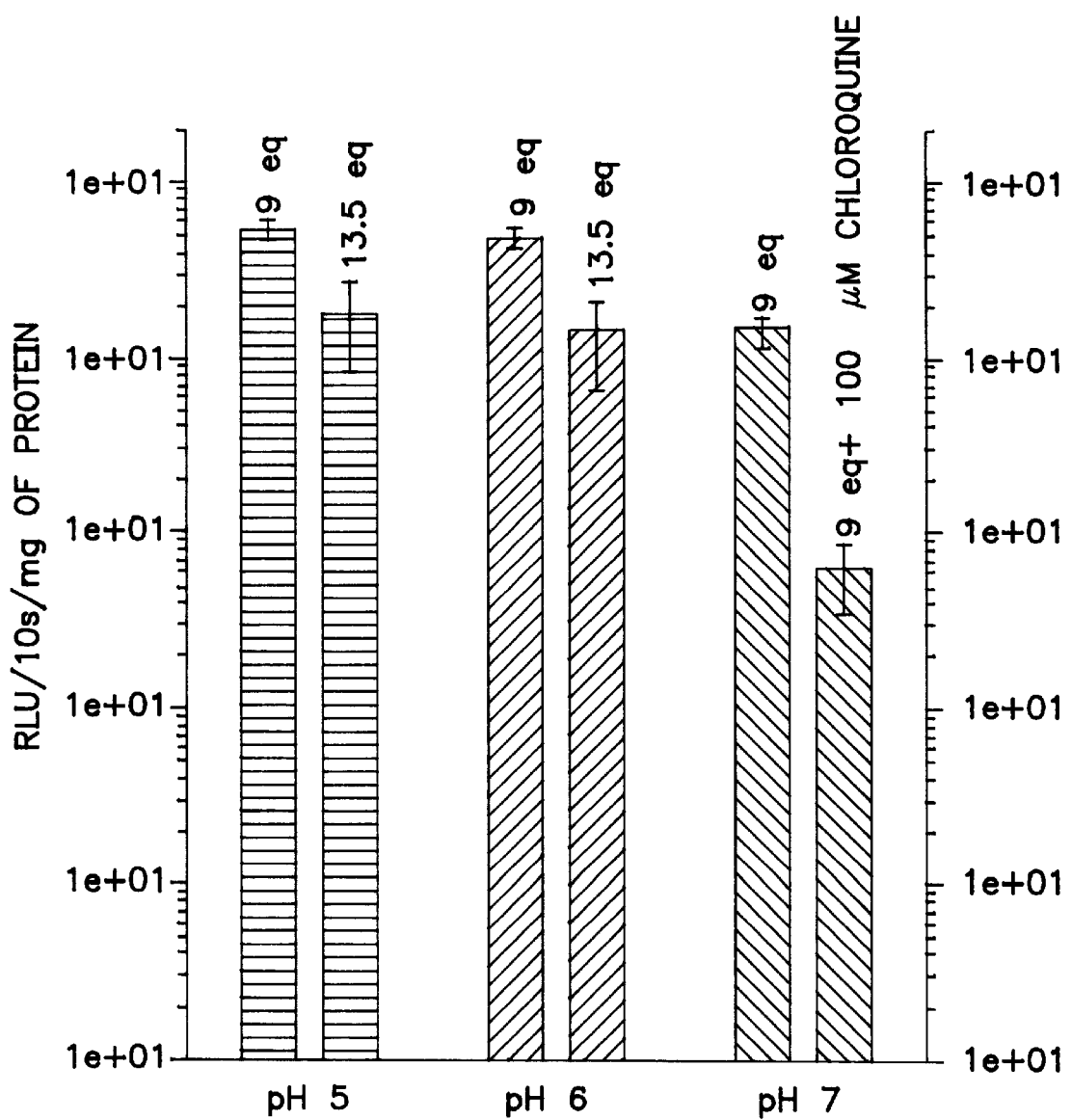
FIG. 4: Efficiency of transfection of PEI800K in terms of pH

The results obtained are presented in FIG. 4. They show that the compositions according to the invention may be used at different pH values, and in particular within physiological pH ranges (pH 5–8).

EXAMPLE 6

Comparison of the Efficiency of Transfection of PEI and of Polylysine

This example describes the comparative results obtained with a composition according to the invention and with another cationic polymer, polylysine, for the transfer of nucleic acids into fibroblasts.

Protocol: The polylysine (PLL) used in this experiment is polylysine.HBr of average weight 50K. The final chloroquine concentration is 100 $\mu$M. The PEI is at pH 6.

Protocol: 3T3 fibroblasts are inoculated into a 24-well dish 18 hours before transfection (50,000 cells per well). They are transfected with plasmid pCMV-Luc according to the protocol used in Example 2. Cells transfected with PLL in the presence of chloroquine are rinsed after 2 hours and placed in medium with 10% of serum. Expression is stopped 24 hours later.

Figure 5:
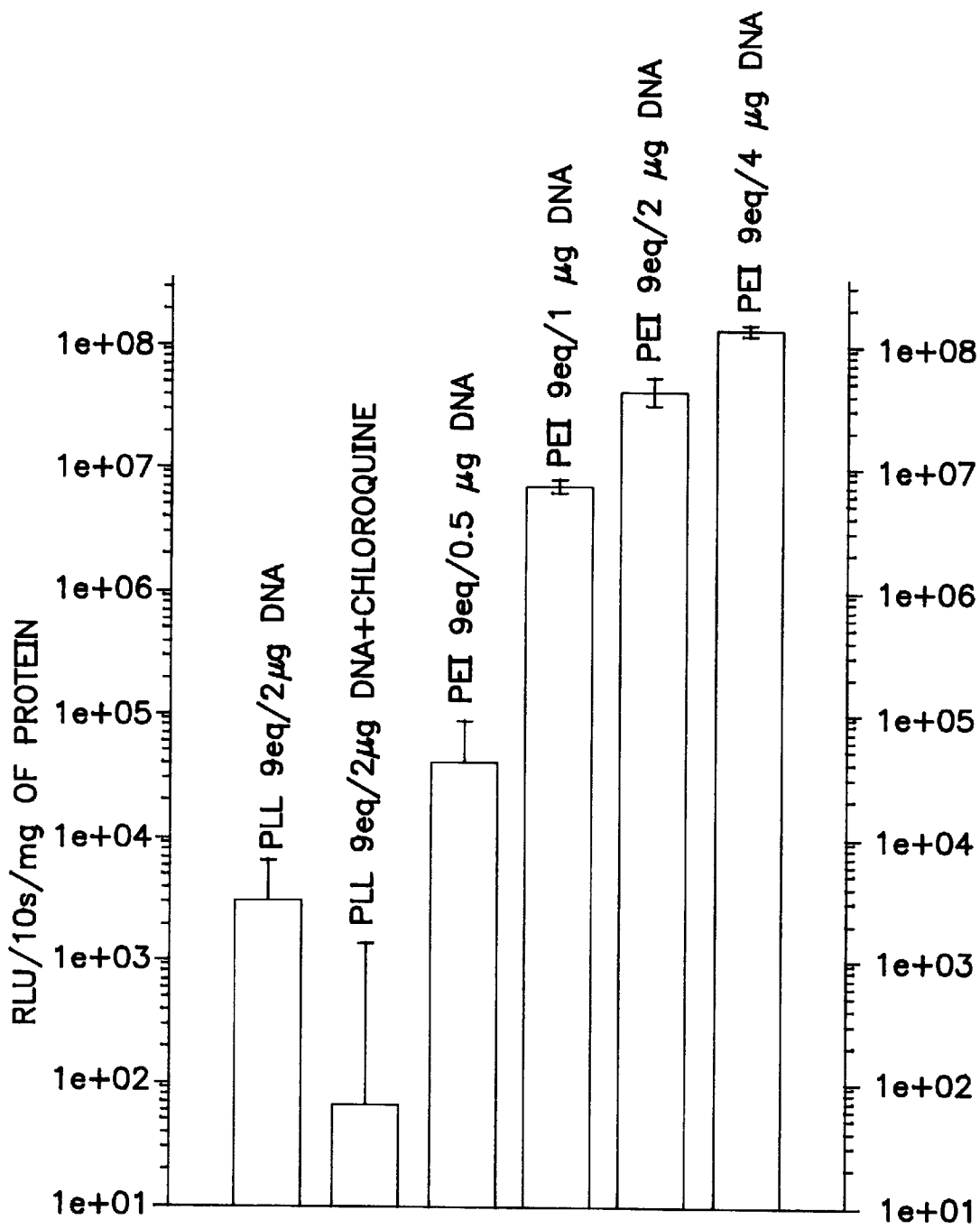
FIG. 5: Comparison between PEI800K and polylysine

The results obtained are presented in FIG. 5. They demonstrate clearly that the compositions according to the invention enable nucleic acids to be transferred into fibroblasts with a much greater efficiency than former cationic polymeric vectors such as polylysine.

EXAMPLE 7

Comparison of the Efficiency of Transfection of NIH 3T3 Fibroblasts with PEI50K and PEI800K This example describes the use and the comparison of two PEI polymers (PEI50K and PEI800K) for the transfer of nucleic acids into cells.

Protocol: Cells are inoculated 24 hours before transfection using 50,000 cells per 16 mm well. They are transfected with the plasmid pCMV-Luc complexed with PEI. The PEI amine/nucleic acid phosphate molar equivalent ratio varies from 6 to 45 equivalents. For each well, the PEI and 2 $\mu$g of DNA are diluted separately in 50 $\mu$l of NaCl (150 mM). The solutions are then mixed and thereafter homogenized. After 10 minutes, this volume is added to the cells. After 24 hours, the cells are lysed, the lysis solution is centrifuged and the supernatant is used for assaying luciferase activity. Protein assay is performed on an aliquot of this supernatant by the BCA test. Luciferase activity is expressed in light units (RLU)/10 seconds of integration/mg of protein.

The results obtained are presented in the table below.

| R | 0 | 6eq | 9eq | 18eq | 45eq |
|---|---|---|---|---|---|
| PEI 50K RLU/10s/mg Prot | 7,100 | 11,000 | 760,000 | 12,000,000 | 2,450,000 |
| PEI 800K RLU/10s/mg Prot | 6,253 | 200,000 | 16,700,000 | 5,650,000 | 525,000 |

These results show clearly that PEI50K possesses transfecting properties which are as advantageous as those of PEI800K.

EXAMPLE 8

Test of Cytotoxicity of PEI

We wanted to study the possible toxicity of PEI50K on NIH 3T3 fibroblasts. For this study we chose the MTT test, which enables the capacity of cells to reduce MTT tetrazolium to MTT formazan by the mitochondrial enzyme succinate dehydrogenase to be evaluated. The transfection protocol is the same as in Example 7 (the amount of DNA per well remains fixed (2 $\mu$g), the number of PEI amine/DNA phospate molar equivalents varies from 9 to 24). After 24 hours of transfection, the cells are washed three times with PBS and then incubated for 90 minutes with 0.05 mg/ml of MTT. At the end of this incubation, the cell medium is removed, and the cells are washed three times with PBS and then dissolved in 1 ml of 10% SDS for 10 minutes. The optical density of the samples is read at 540 nm.

Figure 6:
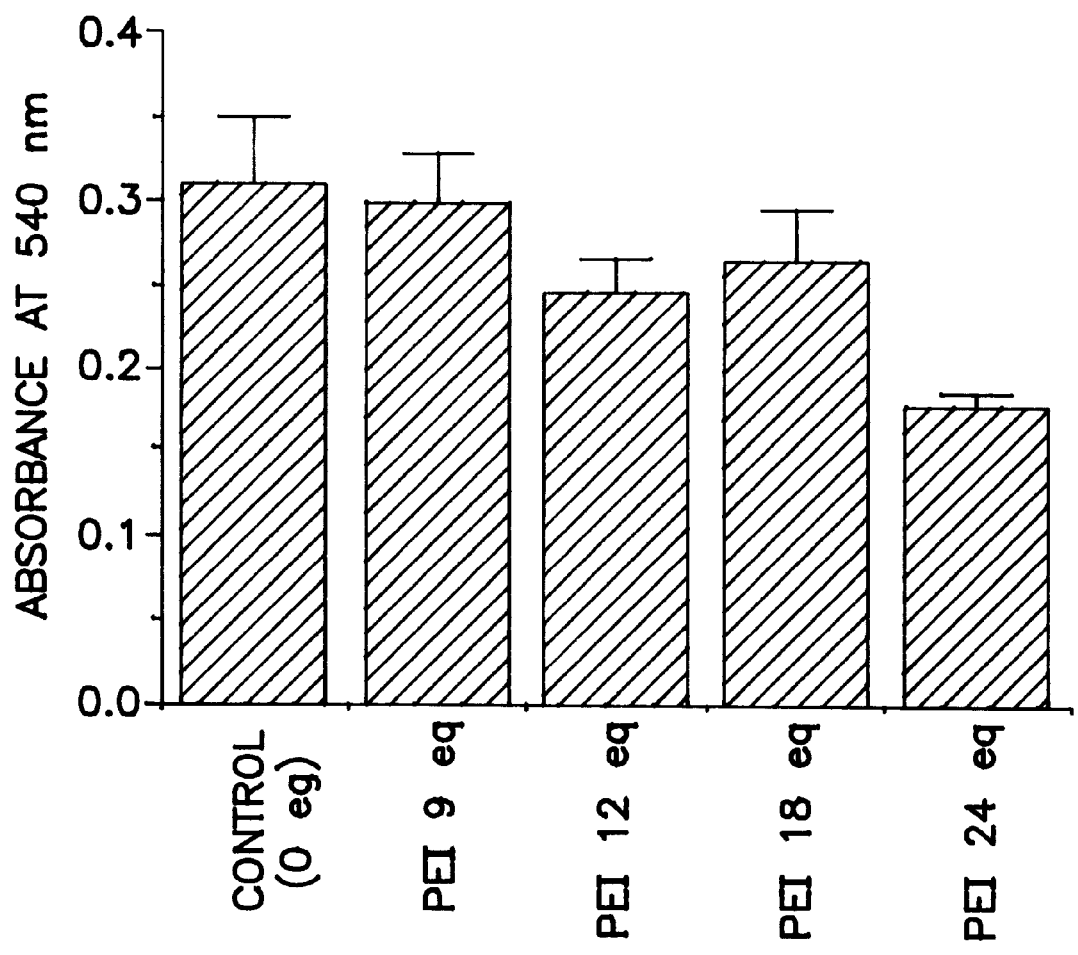
FIG. 6: Test of cytotoxicity of PEI50K

The results are presented in FIG. 6. They show that, under the conditions of our study, PEI50K does not bring about significant mortality for NIH 3T3 fibroblasts.

EXAMPLE 9

Use of an Adjuvant to Improve Transfecting Power

This example describes the use of compositions according to the invention comprising a cationic polymer and an adjuvant. The adjuvant used is either a neutral lipid (DOPE) or a lipopolyamine (DOGS).

Protocol: Addition of DOPE:

Four PEI amine/DNA phosphate molar equivalent ratios were studied: 6, 9, 18 and 21. For each well, 12 nanomoles of DOPE are added to the mixture of PEI and DNA. This solution is then used for transfection as described in Example 7.

Addition of DOGS: For each well, 4 DOGS amine/DNA phosphate molar equivalents (equivalent to 6 nanomoles of DOGS for 6 nanomoles of phosphates) are added to the PEI solution before the step of complexing with the DNA. Transfection is then performed as described in Example 7.

Figure 7:
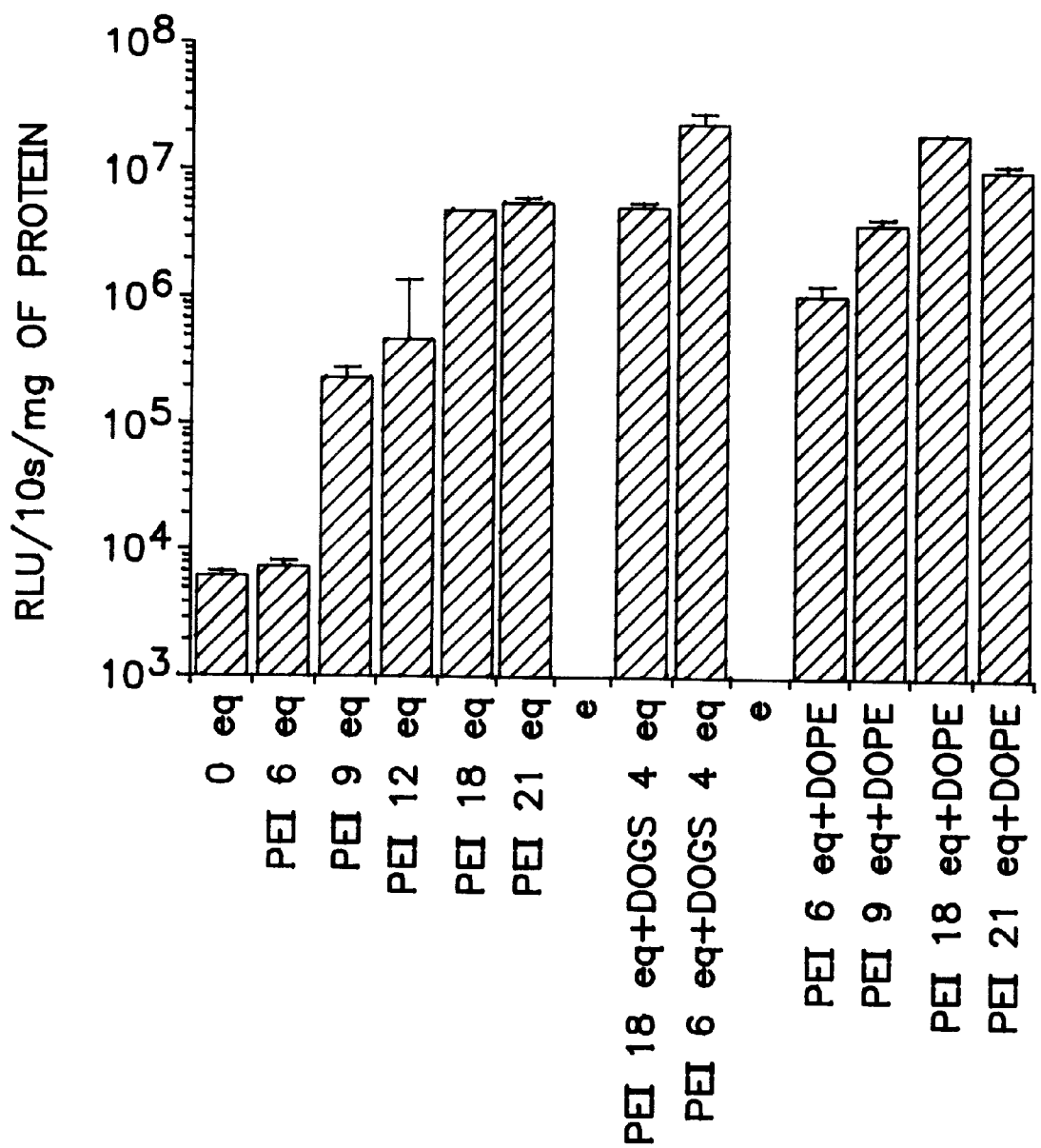
FIG. 7: Efficiency of transfection of PEI50K in the presence of adjuvants

The results obtained are presented in FIG. 7. They show clearly that the addition of DOPE or of DOGS enables the transfection properties to be increased further, in particular for low PEI amine/DNA phosphats molar equivalent ratios.

EXAMPLE 10

Gene Transfer into Hela Cells

This example demonstrates that the compositions according to the invention can be used for the transfer of genes into different cell types, and in particular into Hela uterine carcinoma cells.

Protocol: Hela cells are inoculated 24 hours before transfection using 50,000 cells per 16 mm well. They are then transfected with plasmid pCMV Luc complexed either with PEI or with the lipopolyamine (DOGS). Four PEI50K or PEI800K amine/DNA phosphate molar equivalent ratios were studied: 6, 9, 18, 21. The lipopolyamine is used at 8 amine/phosphate molar equivalents (12 nanomoles of DOGS).

Figure 8A:
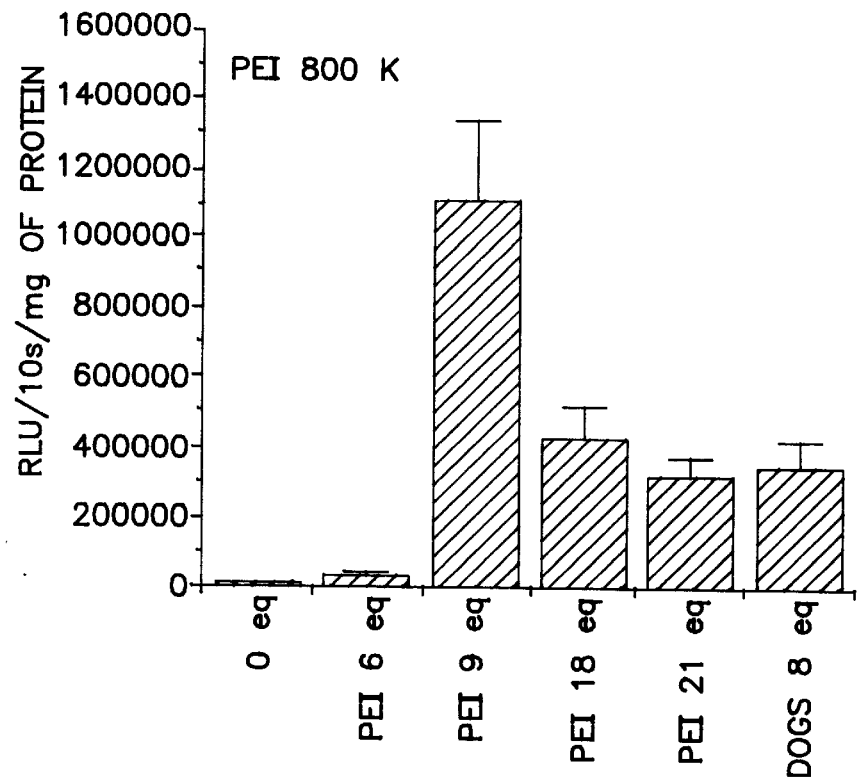
FIGS. 8A–B: Efficiency of PEI for the transfection of HeLa cells
Figure 8B:
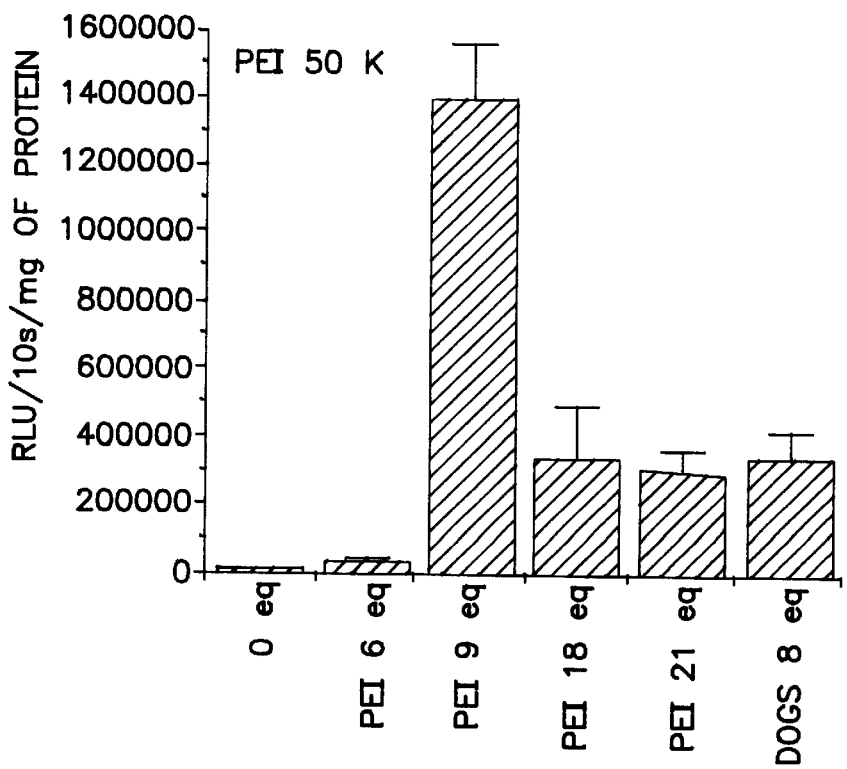

The results obtained are presented in FIG. 8. They show clearly that the compositions according to the invention comprising a cationic polymer optionally combined with an adjuvant enable Hela cells to be transfected much more efficiently than the previous systems (the lipopolyamine DOGS in particular).

EXAMPLE 11

Transfer of Genes into Different Cell Types

This example shows again that the compositions according to the invention can be used for the transfer of genes into a wide variety of cell types, such as fibroblasts, uterine carcinomas, hepatocytomas or kidney cells. More especially, this example describes the transfection of HepG2 and K562 cells and rabbit smooth muscle primary culture cells with PEI containing 9 charge equivalents and at pH 6.

HepG2 cells are inoculated in 24-well dishes 24 hours before transfection (50,000 cells per well). They are transfected with plasmid pCMV-Luc according to the protocol described in Example 2. After 4 hours of transfection, 100 µl of FCS serum are added per well. Expression is stopped 30 hours later.

K562 cells are inoculated in 24-well dishes, in 0.5 ml of RPMI medium without serum one hour before transfection. They are transfected with plasmid pCMV-Luc according to the following protocol: The desired amount of plasmid and the PEI are diluted separately in 50 µl of 150 mM Nacl and mixed. After 10 minutes, the two solutions are combined and homogenized. After a further period of 10 minutes, 400 µl of RPMI are added. The solution thereby obtained is homogenized and, after 10 minutes, it is distributed on the cells. After 4 hours of transfection, 100 µl of FCS serum are added per well. Expression is stopped 30 hours later.

Rabbit smooth muscle primary cultures were prepared as described by Fallier-Becker. The cells were then transfected either with 1 µg or with 2 µg of plasmid pCMV-Luc complexed with PEI (according to the protocol described in Example 7). Expression of luciferase is stopped 24 or 48 hours after transfection.

Figure 9:
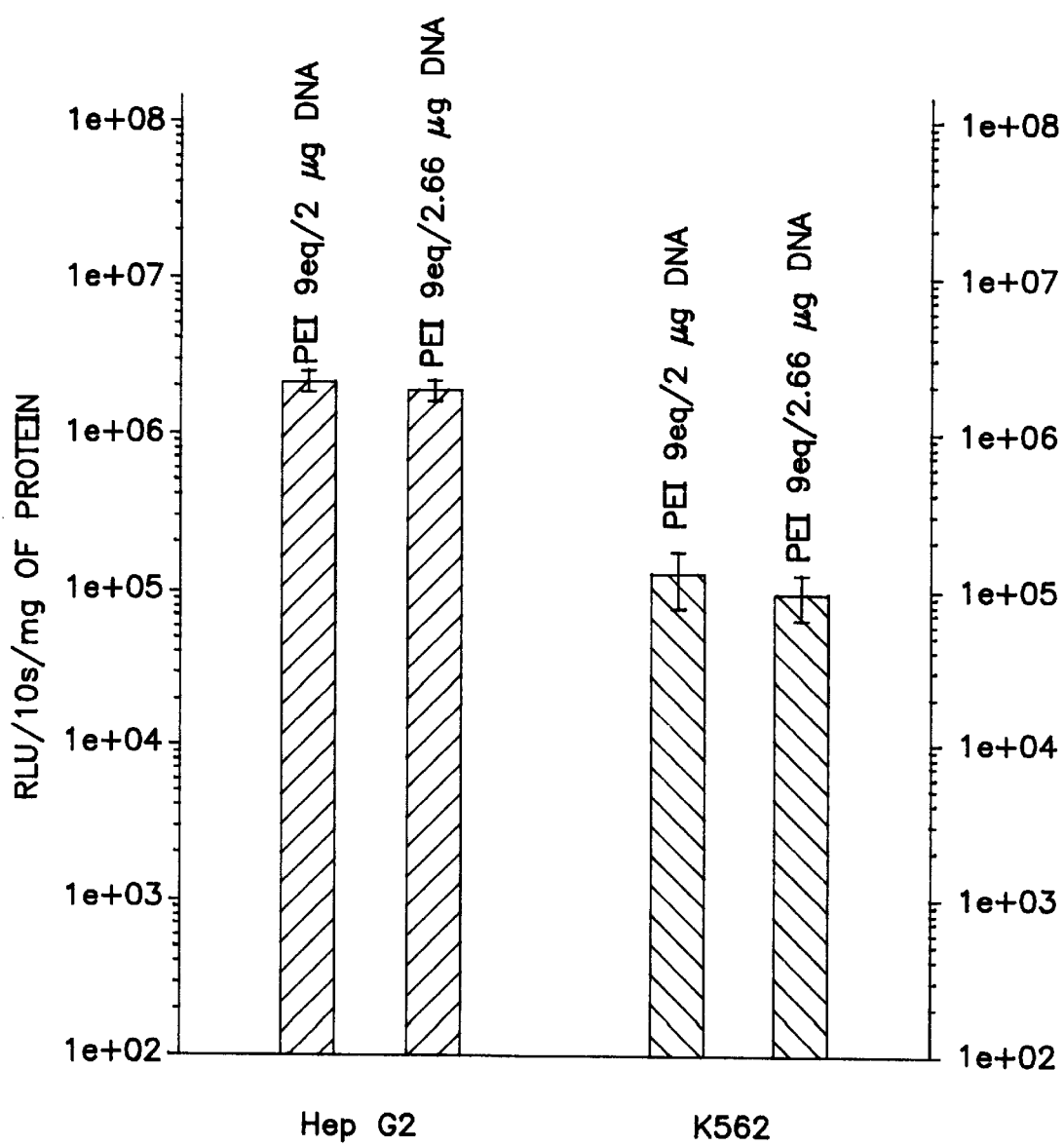
FIG. 9: Efficiency of PEI for the transfection of liver and kidney cells

The results obtained are presented in FIG. 9. They show clearly that the compositions according to the invention permit the efficient transfection of a wide variety of differing cell types.

EXAMPLE 12

Transfer of Plasmid DNA into an Embryonic Neuron Primary Culture: Demonstration of a Biological Activity Neuron primary cultures were prepared as described by Lezoualc'h et al. After 36 h, the cultures were transfected with 2 µg of plasmid TRE-Luc (containing the Luc gene under the control of a thyroid hormone T3 response element) and 0.5 µg of carrier DNA per well.

Two experimental conditions were studied:
  9 equivalents of amines relative to phosphates: 1 µg of plasmid was introduced into 2.28 µl of a 100 mM aqueous solution of PEI800K, pH 7.
  13 equivalents of amines relative to phosphates: 1 µg of plasmid was introduced into 3.33 µl of a 100 mM aqeuous solution of PEI800K, pH 7.

Prior to complexing, the plasmid was diluted in 50 µl of 150 mM NaCl, and the PEI was also diluted in a second 50 µl aliquot of 150 mM NaCl. The solutions were then mixed and applied to the cells for 1 h. The transfection medium was then removed and replaced by fresh culture medium, with or without T3 (1 nM). After 24 h, the cells were lysed, the lysis solution was centrifuged and the supernatant was used for assaying luciferase activity.

Figure 10:
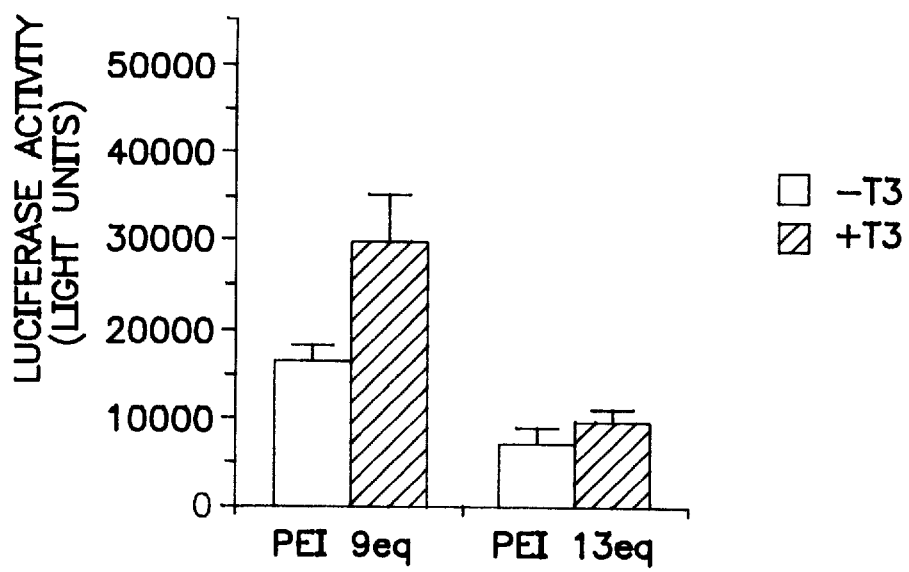
FIG. 10: Efficiency of PEI for the transfer of plasmid DNA into embryonic neurons

The results obtained are presented in FIG. 10. They show clearly that the compositions according to the invention enable DNA to be transferred into neuronal cells, and that the DNA thus transferred is functional since its activity is amplified in the presence of T3. In the control experiment performed in the presence of the plasmid alone, no luciferase activity was detected.

EXAMPLE 13

Transfer of Antisense Oligonucleotides into an Embryonic Neuron Primary Culture Experiments were carried out on neuron primary cultures prepared as in Example 12. After 36 h, the cultures were transfected with 2 µM 18mer antisense oligonucleotide (ODN) complexed with 9 equivalents of amines relative to the PEI800K phosphates.

The ODN used is directed against a region of the gene coding for the thyroid hormone alpha-receptor. Its sequence is as follows:

5'-GCTGGGCTTCTGTTCCAT-3

For 4 wells of 250 µl of culture medium, the following products were used:
  8 µl of a 0.25 mM solution of ODN diluted in 10 µl of 150 mM NaCl, and
  20.8 µl of a 12 mM aqueous solution of PEI800K, pH7, previously diluted in a second 51.2 µl aliquot of 150 mM NaCl.

The solutions were then mixed, and 20 µl of the mixture were applied to the cells for 45 min. The transfection medium was then removed and replaced by fresh culture medium. The cells were then fixed in 4% paraformaldehyde solution, rinsed, mounted in Mowiol and examined under a fluorescence microscope.

Figure 11A:
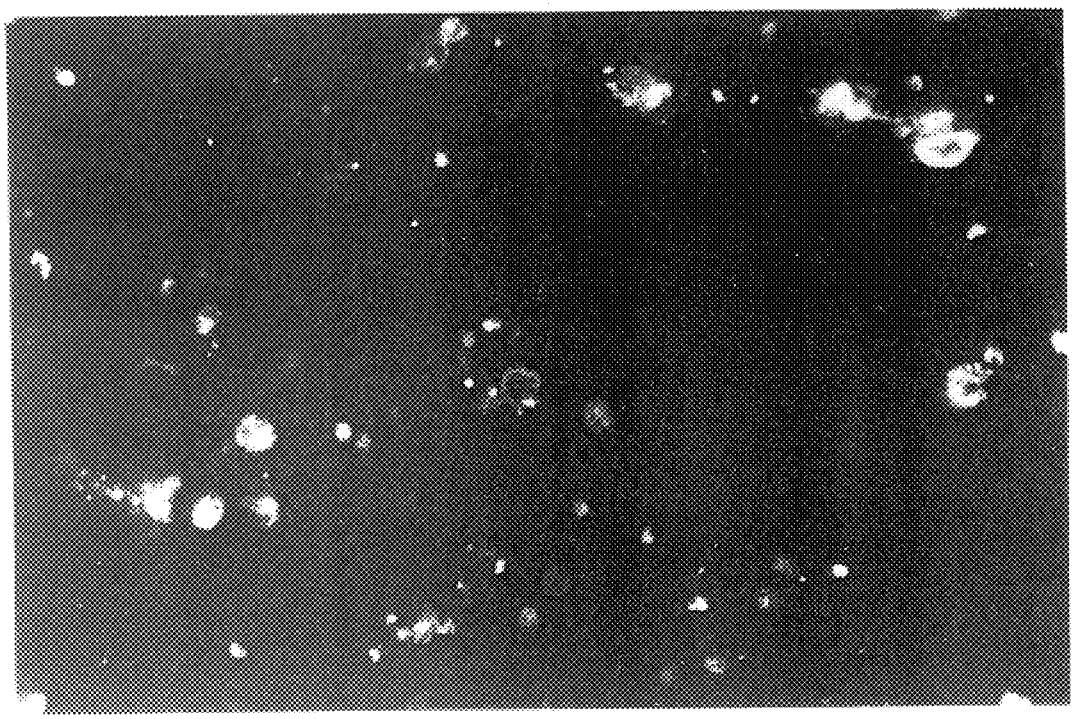
FIGS. 11A–B: Efficiency of PEI for the transfer of oligonucleotides into embryonic neurons
Figure 11B:
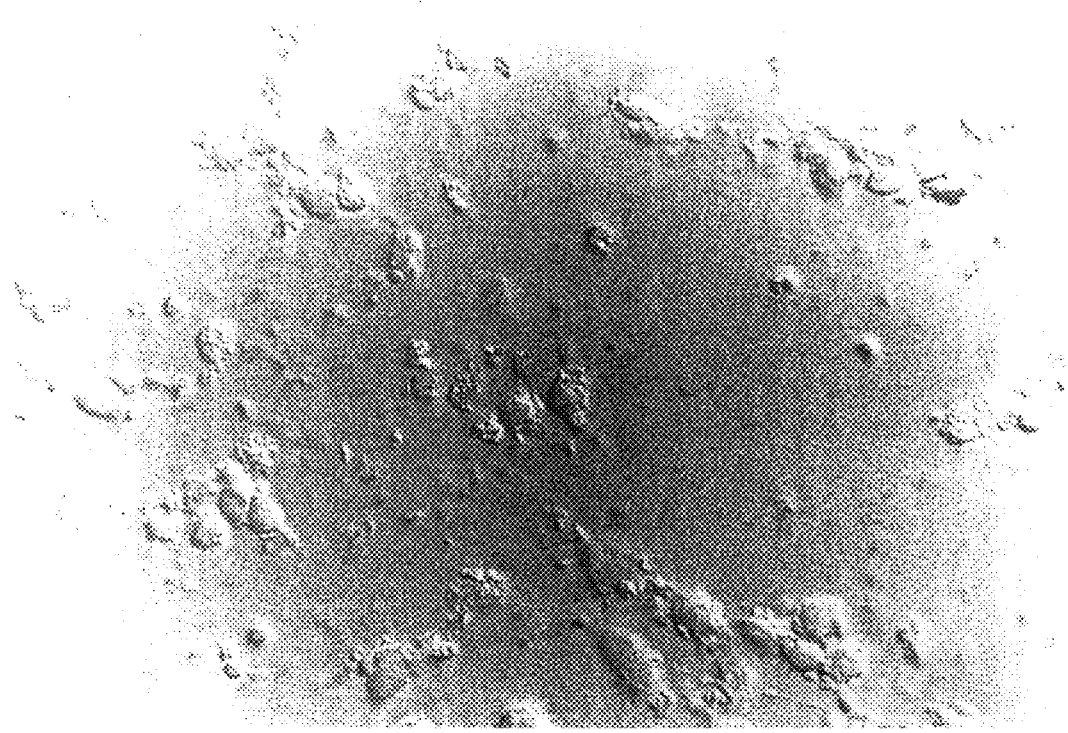

The results obtained are presented in FIG. 11. They show clearly that the compositions according to the invention enable antisense oligonucleotides to be transferred into neuronal cells. In the control experiment performed in the presence of the oligonucleotide alone, no fluorescence was detected.

EXAMPLE 14

Use of the Compositions of the Invention for the Transfer of Nucleic Acids in vivo Into the Brain of Newborn Mice This example describes the transfer of plasmid pCMV-Luc in vivo into the brain of newborn mice. It demonstrates the especially advantageous properties of the compositions according to the invention, in particular for gene therapy applications.

30 µg of plasmid pCMV-luc (7.5 µl of a stock solution containing 4 µg/µl) were diluted in 22.5 µl of sterile 5% glucose (final concentration 1 µg/µl). 8.5 µl of 100 mM PEI800K (prepared in water and buffered to pH 6.9) were then added. The composition thereby obtained hence contains 9 equivalents of amines relative to phosphates.

The mixture was vortexed rapidly and used for intracerebral injections in newborn mice. To this end, the mice were anaesthetized by cold (placed on an aluminium foil in contact with ice), and 2 µl of mixture (2 µg of nucleic acid) were then injected per mouse. Injections were carried out into the cortex using a micromanipulator and a microsyringe, both connected to a microelectrode.

The brains were removed 48 hours later, homogenized and centrifuged, and the supernatant was used for the assay of luciferase. To this end, the supernatant was incubated in the presence of a buffer comprising luciferin, coenzyme A and ATP, and the light emitted (generally for 10 seconds) was measured with a luminometer (Wood K. (1990) Promega Notes, 28).

Figure 12:
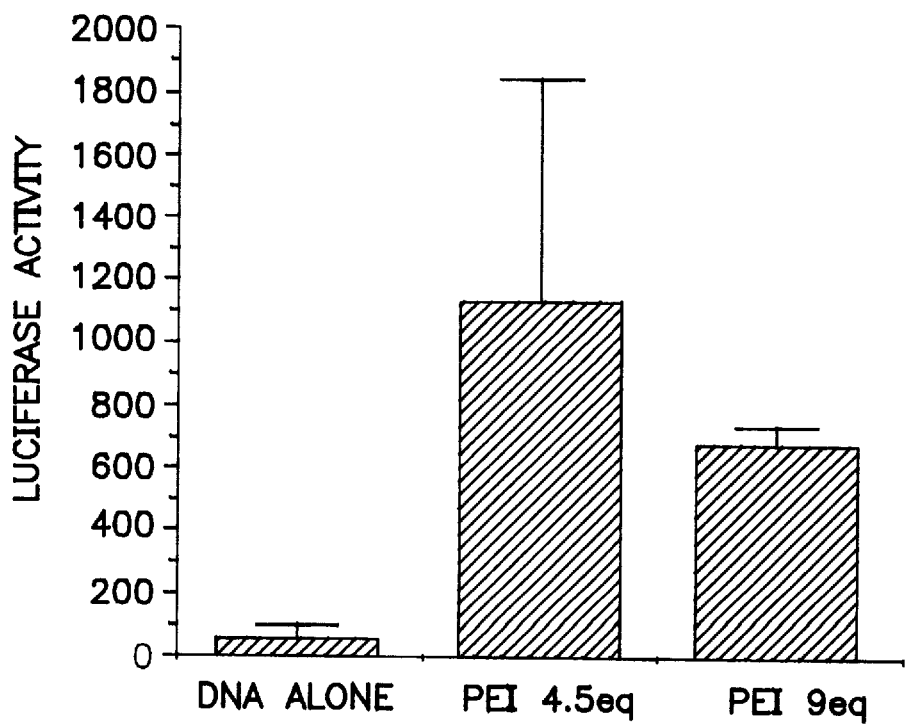
FIG. 12: Efficiency of PEI for in vivo DNA transfer

The results obtained are presented in FIG. 12. They show clearly that the compositions enable the plasmid to be transferred efficiently into the brain of mice, whereas no significant luciferase activity is observed when the transfer is carried out by means of the plasmid alone.

7. A composition according to claim 6, wherein the ratio is between 2 and 50.

8. A composition according to claim 7, wherein the ratio is between 5 and 30.

9. A composition according to claim 1, comprising one or more adjuvants capable of combining with a complex between the polymer and nucleic acid, and of improving the transfer of the nucleic acid into cells.

10. A composition according to claim 9, wherein the adjuvant comprises a lipid, protein, lipopolyamine or synthetic polymer.

We claim:

1. A composition comprising at least one nucleic acid and a cationic polymer of general formula (I):

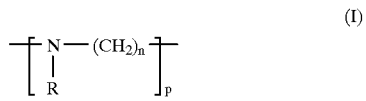

in which

R is a hydrogen atom or a group of formula

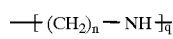

wherein the R group is attached at the ($CH_2$) end to the N atom in the main formula;

n is an integer between 2 and 10;

p and q are integers, wherein the sum of p+q is such that the average molecular weight of the polymer is between 100 and $10^7$.

2. A composition according to claim 1, wherein n is between 2 and 5.

3. A composition according to claim 1, wherein the polymer has an average molecular weight between $10^3$ and $5 \times 10^6$.

4. A composition according to claim 1, wherein the polymer is selected from the group consisting of polyethylenimine (PEI) and polypropylenimine (PPI).

5. A composition according to claim 4, wherein the polyethylenimine has an average molecular weight 50,000 (PEI50K) or 800,000 (PEI800K).

6. A composition according to claim 1, wherein the polymer amines to nucleic acid phosphates ratio is between 0.5 and 50.

11. A composition according to claim 10, wherein the lipid is a cationic lipid.

12. A composition according to claim 11, wherein the cationic lipid is one or more lipopolyamines.

13. A composition according to claim 12, wherein the lipopolyamine has the general formula $H_2N$—(—$(CH)_m$—NH—)l—H, in which m is an integer greater than or equal to 2 and l is an integer greater than or equal to 1, wherein m may vary between different carbon groups between two amines.

14. A composition according to claim 13, wherein the lipopolyamine is dioctadecylamidoglycylspermine (DOGS) or palmitoylphosphatidylethanolamine 5-carboxyspermylamide (DPPES).

15. A composition according to claim 10, wherein the lipid is one or more neutral lipids.

16. A composition according to claim 15, wherein the neutral lipid is a synthetic or natural lipid which is zwitterionic or lacks ionic charge under physiological conditions.

17. A composition according to claim 16, wherein the neutral lipid contains two fatty chains.

18. A composition according to claim 16, wherein the neutral lipid is selected from the group consisting of dioleoylphosphatidylethanolamine (DOPE), oleoylpalmitoylphosphatidylethanolamine (POPE), distearoylphosphatidyl-ethanolamine, a 1- to 3-fold N-methylated derivative of distearoylphosphatidyl-ethanolamine, dipalmitoylphosphatidyl-ethanolamine, a 1- to 3-fold N-methylated derivative of dipalmitoylphosphatidyl-ethanolamine, dimyristoylphosphatidyl-ethanolamine, a 1- to 3-fold N-methylated derivative of dimyristoylphosphatidyl-ethanolamine, phosphatidylglycerol, diacylglycerol, glycosyldiacylglycerol, a cerebroside, a sphingolipid or an asialoganglioside.

19. A composition according to claim 18, wherein the cerebroside is a galactocerebroside.

20. A composition according to claim 18, wherein the sphingolipid is a sphingomyelin.

21. A composition according to claim 18, wherein the asialoganglioside is asialoGM1 or asialoGM2.

22. A composition according to claim 1, wherein the nucleic acid is a deoxyribonucleic acid.

23. A composition according to claim 1, wherein the nucleic acid is a ribonucleic acid.

24. A composition according to claim 1, wherein the nucleic acid is chemically modified.

25. A composition according to claim 1, wherein the nucleic acid is an antisense sequence.

26. A composition according to claim 1, wherein the nucleic acid comprises a therapeutic gene.

27. A composition according to claim 9, comprising from 0.1 to 20 molar equivalents of adjuvant per molar equivalent of nucleic acid phosphates.

28. A composition according to claim 27, comprising from 1 to 5 molar equivalents of adjuvant per molar equivalent of nucleic acid phosphates.

29. A composition according to claim 1, comprising a targeting element.

30. A composition according to claim 29, wherein the targeting element comprises a sugar, peptide, antibody, antibody fragment, cell receptor ligand or fragment thereof, receptor or receptor fragment.

31. A composition according to claim 29, wherein the targeting element is bound covalently to the polymer of formula (I).

32. A composition according to claim 1, comprising a vehicle which is pharmaceutically acceptable for an injectable formulation.

33. A composition according to claim 1, comprising a vehicle which is pharmaceutically acceptable for application to the skin and/or the mucosae.

34. A method of transferring a nucleic acid into cells comprising administering to said cells a composition according to claim 1.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide"

(xi) SEQUENCE DESCRIPTION: SEQ ID NO:1:

GCTGGGCTTC TGTTCCAT                                                          18